US00PP13274P3

(12) United States Plant Patent
Noodelijk

(10) Patent No.: US PP13,274 P3
(45) Date of Patent: Nov. 26, 2002

(54) CHRYSANTHEMUM PLANT NAMED 'MEDEA'

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 0 days.

(21) Appl. No.: 09/734,657

(22) Filed: Dec. 13, 2000

(65) Prior Publication Data

US 2002/0073459 P1 Jun. 13, 2002

(51) Int. Cl.[7] ..... A01H 5/00

(52) U.S. Cl. ..... Plt./296

(58) Field of Search ..... Plt./296

*Primary Examiner*—Bruce R. Campell
*Assistant Examiner*—Anne Marie Grünberg
(74) *Attorney, Agent, or Firm*—Parkhurst & Wendel, L.L.P.

(57) ABSTRACT

A chrysanthemum plant named 'MEDEA' characterized by its small sized blooms with apricot ray florets and prolific branching; natural season flower date August 21–27; blooming for a period of 4 weeks.

3 Drawing Sheets

BACKGROUND OF THE INVENTION

'MEDEA' is a product of a breeding and selection program for outdoor pot mums (garden mums) which had the objective of creating new chrysanthemum cultivars with a daisy type flower, a natural season flower date around August 21–27; blooming for a period of 4 weeks. The new plant of the present invention comprises a new and distinct cultivar of Chrysanthemum plant 'MEDEA' is a seedling resulting from the open pollination among groups of chrysanthemum cultivars maintained under the control of the inventor for breeding purposes. The new and distinct cultivar was discovered and selected as one flowering plant by Rob Noodelijk on a cultivated field in Rijsenhout, Holland in September 1998. The plant has been asexually reproduced by cuttings in greenhouses at Rijsenhout, Holland. The new cultivar has been found to retain its distinctive characteristics through successive propagations.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
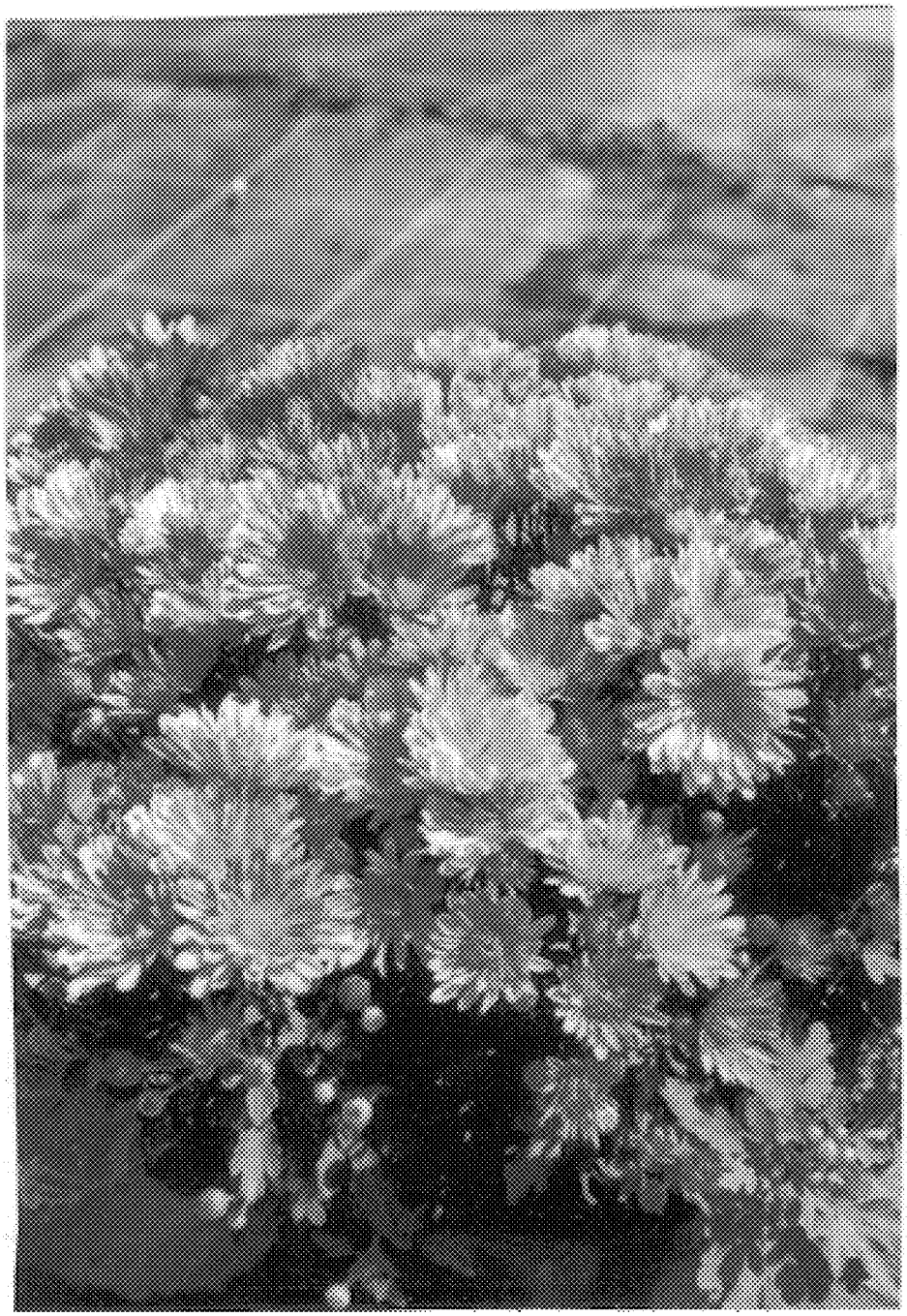
FIG. 1 shows a plant of the cultivar in full bloom.
Figure 2:
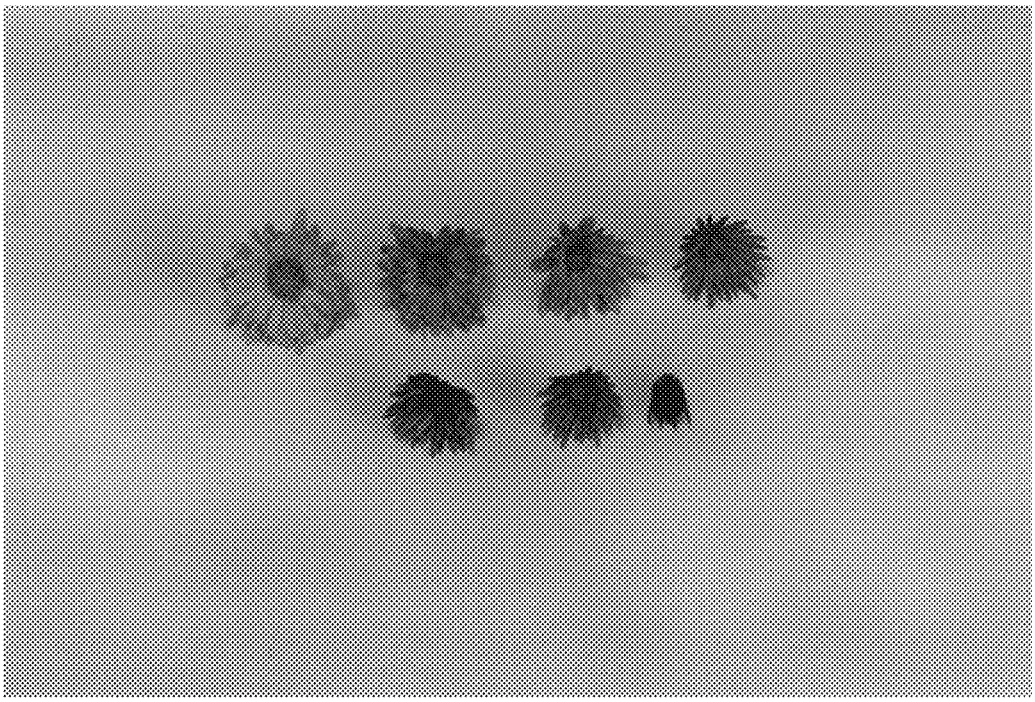
FIG. 2 shows the various stages of bloom of the new cultivar.
Figure 3:
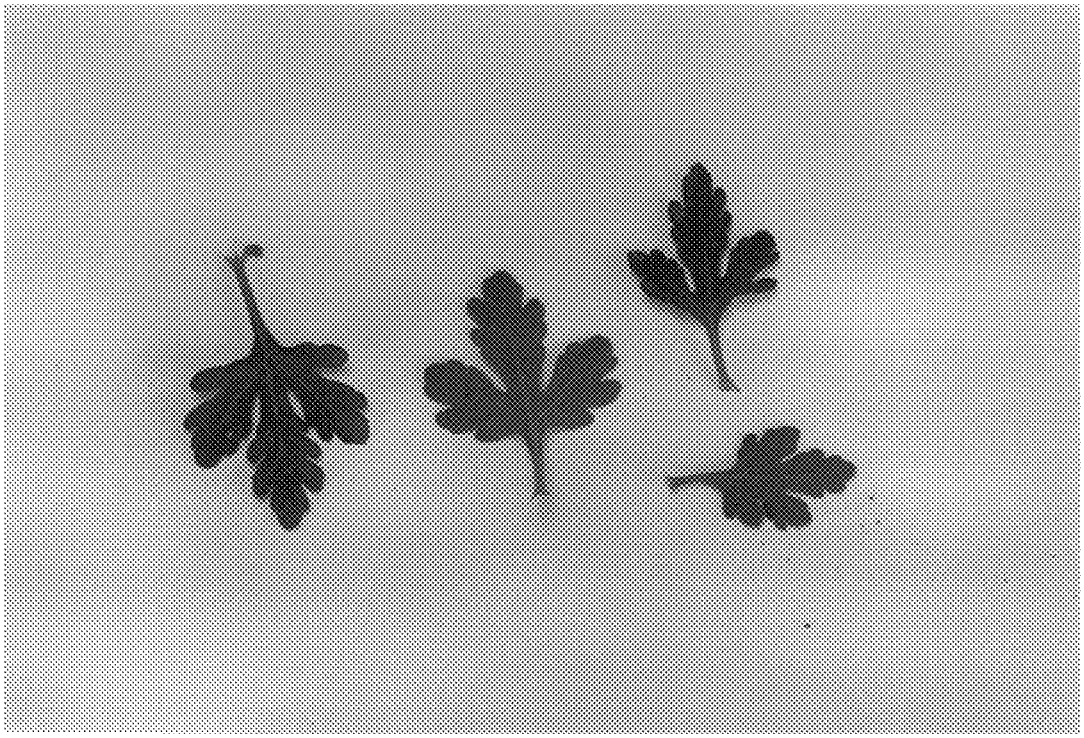
FIG. 3 shows the various stages of foliage and petiole of the new cultivar.

This new variety of chrysanthemum is of the botanical classification *Chrysanthemum morifolium*. The observations and measurements were gathered from plants grown out door in Rijsenhout, Holland under natural day length and temperature and planted week 22 in 1999 and 2000. The natural blooming date of this crop was August 21–27 (week 34). The average height of the plants was 36–40 cms. No growth retardants were used. No tests were done on disease or insects resistance or susceptibility. No tests were done on cold or drought resistance. This new variety produces small sized blooms with apricot ray florets and a yellow-orange disc-florets blooming for a period of 4 weeks.

From the cultivars known to inventor the most similar existing cultivar in comparison to 'MEDEA' is 'WARM MEGAN' (U.S. Plant Pat. No. 9,126). When 'WARM MEGAN' and 'MEDEA' are being compared the following differences are noticed: The differences of 'WARM MEGAN' and 'MEDEA' are (1) Natural blooming date. 'MEDEA' flowers much earlier (2) Flower color. The color of 'WARM MEGAN' is comparable but darker.

The following is a description of the plant and characteristics that distinguish 'MEDEA' as a new and distinct variety.

The color designations are taken from the plant itself. Accordingly, any discrepancies between the color designations and the colors depicted in the photographs are due to photographic tolerances. The color chart used in this description is: The Royal Horticultural Society color chart, edition 1995.

Table 1: Botanical Description of Cultivar 'Medea'

Bud:
- *Size.*—Small; cross-section 1.0 cm, height 1.1 cm.
- *Outside color.*—Greyed-orange 176 A.
- *Involucral bracts.*—2 rows, length 7 mm, width 3 mm.
- *Involucral bracts among disc-florets.*—Not present.
- *Involucral bracts color.*—Green 138 B.

Bloom:
- *Type.*—Daisy.
- *Height.*—Flat, 1.1–1.3 cm.
- *Size.*—Small.
- *Fully expanded.*—4.0 cm.
- *Number of blooms per branch.*—Approx. 7 blooms per branch.
- *Performance on the plant.*—4 weeks.
- *Seeds (if crossed).*—Produced in large quantities, oval shaped. Grey-brown 199 A, 1.5 mm in length.
- *Fragrance.*—Typical chrysanthemum, slight.

Color:

*Center of the flower* (*disc-florets*).—Immature yellow-green 153 A. Mature yellow-orange 14 A.

*Color of upper surface of the ray-florets.*—Greyed-orange 165 D.

*Color of the lower surface of the ray-florets.*—Greyed-orange 166 D.

*Tonality from distance.*—A garden mum with apricot flowers and a yellow-orange disc.

*Color of the upper surface of the flowers after aging of the plant.*—Greyed-orange 164 D.

Ray florets:

*Texture.*—Upper and under side smooth.

*Number.*—55–60.

*Cross-section.*—Flat, sometimes concave.

*Longitudinal axis of majority.*—Straight sometimes incurved.

*Length of corolla tube.*—Very short, 0.3–0.5 cm.

*Ray-floret margin.*—Entire.

*Ray-floret length.*—1.5–1.8 cm.

*Ray-floret width.*—0.3–0.6 cm.

*Ratio length/width.*—Medium.

*Shape of tip.*—Rounded.

Disc florets:

*Disc diameter.*—0.8 cm.

*Distribution of disc florets.*—Numerous, clearly visible at all stages of flowering.

*Shape.*—Tubular.

*Color.*—Yellow-green 153 A.

*Receptacle shape.*—Conical raised.

Reproductive organs:

*Stamen* (*present in disc florets only*).—Thin, 2 mm in length.

*Stamen color.*—Yellow 12 A.

*Pollen.*—Present.

*Pollen color.*—Yellow 12 A.

*Styles.*—Thin.

*Style color.*—Yellow-green 144 A.

*Style length.*—3 mm.

*Stigmas.*—Yellow-green 144 A.

*Stigma width.*—1 mm.

*Ovaries.*—Enclosed in calyx.

Plant:

*Shape.*—Grown as a spray-type pot-mum, outdoor rounded.

*Growth habit.*—Spreading.

*Growth rate.*—Moderate.

*Height.*—36–40 cm.

*Width.*—35–40 cm.

*Stem color.*—Green 138 B.

*Stem strength.*—Medium.

*Stem brittleness.*—Absent.

*Stem anthocyanin coloration.*—Present, a thin layer of greyed-red 181 A mainly at the base of the stem.

*Length of lateral branch.*—From top to bottom 17–19 cm.

*Lateral branch color.*—Green 138 B.

*Lateral branch, attachment.*—Strong.

*Branching* (*average number of lateral branches*).—Prolific with 9–11 breaks after pinching.

*Peduncle length.*—2.5–3.0 cm.

*Peduncle color.*—Green 138 B.

*Natural season blooming date.*—August 21–27.

Foliage:

*Color of mature leaves.*—Upper side yellow-green 146 B. Under side yellow-green 146 C.

*Color of immature leaves.*—Upper side green 137 A. Under side green 137 C.

*Size.*—Very small; length 4.0 cm, width 3.5 cm.

*Quantity* (*number per lateral branch*).—9–11.

*Shape.*—Ovate.

*Texture upper side.*—Glabrous.

*Texture under side.*—Pubescent.

*Venation arrangement.*—Palmate.

*Shape of the margin.*—Serrated.

*Shape of base of sinus between lateral lobes.*—Acute.

*Margin of sinus between lateral lobes.*—Converging.

*Shape of base.*—Truncate sometimes asymmetrical.

*Apex.*—Cuspidate.

TABLE 2

Differences with the comparison varieties (when grown under the same conditions)

| | 'MEDEA' | 'WARM MEGAN' |
|---|---|---|
| Natural blooming date | 21–27 August | 20–26 September |
| (Flower color) Color of the upper surface of the ray-florets | Greyed-orange 165 D | Greyed-orange 173 B |

I claim:

1. A new and distinct variety of chrysanthemum plant as described and illustrated.

* * * * *